(12) United States Patent
Allen

(10) Patent No.: US 10,821,305 B2
(45) Date of Patent: Nov. 3, 2020

(54) RADIOTHERAPY CALIBRATION

(71) Applicant: Elekta Limited, West Sussex (GB)

(72) Inventor: John Allen, West Sussex (GB)

(73) Assignee: ELEKTA LIMITED, West Sussex (GB)

( * ) Notice: Subject to any disclaimer, the term of this patent is extended or adjusted under 35 U.S.C. 154(b) by 485 days.

(21) Appl. No.: 15/598,377

(22) Filed: May 18, 2017

(65) Prior Publication Data

US 2017/0348546 A1 Dec. 7, 2017

(30) Foreign Application Priority Data

Jun. 1, 2016 (GB) .................................. 1609588.7

(51) Int. Cl.
*A61N 5/10* (2006.01)
*G01T 3/00* (2006.01)

(52) U.S. Cl.
CPC .......... *A61N 5/1075* (2013.01); *A61N 5/1067* (2013.01); *G01T 3/00* (2013.01); *A61N 5/1065* (2013.01); *A61N 2005/109* (2013.01); *A61N 2005/1089* (2013.01)

(58) Field of Classification Search
CPC ...... A61N 2005/1089; A61N 2005/109; A61N 5/1065; A61N 5/1067; A61N 5/1075; A61N 2005/1087; A61N 5/10; A61N 2005/1052; A61N 5/1048; A61N 5/1079; A61N 5/1064; A61N 5/1081; A61N 2005/1058; A61N 2005/1076; A61N 5/1043; A61N 5/1084; A61N 2005/1055; A61N 2005/1091; A61N 2005/1098; A61N 5/1039; A61N 5/1077; A61N 5/1042; A61N 5/1049; G01T 3/00; G01T 1/167; G01T 1/29; G01T 5/06; G01T 3/001; G01T 3/065; G01T 1/295; G01V 5/0091; G01V 5/08; G01N 23/005; G01N 23/203; G01N 23/204; G01N 23/22; G21K 1/043; G21K 5/04; A61B 6/037; A61B 6/4258; A61B 6/583; H05H 13/04
USPC ....... 378/64, 65, 143, 207; 250/367, 390.01, 250/390.04, 358.1
See application file for complete search history.

(56) References Cited

U.S. PATENT DOCUMENTS

| | | | |
|---|---|---|---|
| 8,198,587 B2 * | 6/2012 | Whittum .............. | G01N 23/083 250/306 |
| 8,610,080 B2 * | 12/2013 | Lyoussi ..................... | G01T 3/00 250/390.01 |
| 2007/0295911 A1 * | 12/2007 | Sved ........................ | G01T 3/00 250/359.1 |

(Continued)

FOREIGN PATENT DOCUMENTS

EP   2979728 A1   2/2016
JP   2015082376 A  4/2015

*Primary Examiner* — Irakli Kiknadze
(74) *Attorney, Agent, or Firm* — Finnegan, Henderson, Farabow, Garrett & Dunner, L.L.P.

(57) ABSTRACT

A radiotherapy apparatus is disclosed, with a linear accelerator for producing a beam of electrons, a target aligned with the electron beam, the target being capable of producing photons when electrons are incident thereon, and a material which is capable of producing neutrons when photons of sufficient energy are incident thereon. A neutron detector capable of providing a signal to a controller of the linear accelerator is provided, the controller being capable of varying the energy of the electrons of the electron beam.

19 Claims, 3 Drawing Sheets

(56) References Cited

U.S. PATENT DOCUMENTS

| | | | |
|---|---|---|---|
| 2010/0046690 A1* | 2/2010 | Proctor | G01V 5/0091 |
| | | | 376/154 |
| 2010/0258732 A1* | 10/2010 | Rodriguez | A61N 5/1048 |
| | | | 250/370.05 |
| 2011/0180718 A1* | 7/2011 | Luszik-Bhadra | G01T 3/00 |
| | | | 250/390.03 |
| 2011/0266452 A1 | 11/2011 | Lyoussi et al. | |
| 2012/0294423 A1* | 11/2012 | Cheung | H05H 7/12 |
| | | | 378/65 |
| 2014/0270034 A1* | 9/2014 | Clayton | G01V 5/0091 |
| | | | 376/154 |

\* cited by examiner

RADIOTHERAPY CALIBRATION

CROSS-REFERENCE TO RELATED PATENT APPLICATIONS

This application claims the benefit and priority of prior United Kingdom Patent Application No. 1609588.7, filed on Jun. 1, 2016, the entire contents of which are incorporated by reference herein.

FIELD OF THE INVENTION

The present invention relates to radiotherapy apparatus, especially radiotherapy apparatus in which treatment radiation is generated by a linear accelerator.

BACKGROUND ART

In radiotherapy, a treatment is usually planned in advance of the treatment taking place. A treatment plan must take into account the dose level which can be provided by a radiotherapy apparatus. It is vital that a patient does not receive too much radiation, as the consequences of doing so can be severe; it is also important that the patient receives the planned amount of radiation to ensure efficacy of the treatment.

A long-standing challenge in the field has been to provide a radiotherapy apparatus which can provide a predictable and stable dose level to a patient. One factor of the dose level which can be provided by a particular radiotherapy apparatus is the energy spectrum of photons, for example X-rays, provided by a radiotherapy device, usually characterised by its peak energy. Currently, medical physicists in a hospital or clinic often perform commissioning tests on new radiotherapy equipment. Alternatively, a manufacturer of radiotherapy equipment may aim to provide equipment which has a stated maximum dose level, upon which a medical practitioner can rely, which is sometimes referred to as gold standard data. However, both commissioning tests and gold standard data require external test equipment because linear accelerators, which are often used to generate photons, are generally not capable of checking their output to the degree of accuracy required.

SUMMARY OF THE INVENTION

Linear accelerators generally provide a beam of electrons which have been accelerated to a certain energy level. Approximately, a high proportion of electrons provided by a particular configuration of a linear accelerator are accelerated to substantially the same energy level. Thus, linear accelerators are often described in terms of the energy of the electrons provided. The energetic electrons are usually accelerated towards a target, the target subjecting the electrons to rapid deceleration, and thus producing "bremsstrahlung", electromagnetic radiation in the form of photons, usually X-rays. The "bremsstrahlung" photons are not all of the same energy: there is generally a relatively broad distribution of energies of the photons produced. No photons generated by the electron hitting the target can have an energy which exceeds the energy of the electrons provided to the target, though.

Some materials can be affected by the incidence of energetic photons incident thereon, sometimes referred to as a (γ,n) reaction, so that an incident photon can liberate a neutron out of the nucleus of an atom of that material. A general description of such a transition may be:

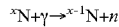

$$^{x}N+\gamma \rightarrow {}^{x-1}N+n$$

where x is the mass number of the nucleus N (i.e. the total number of protons and neutrons in the nucleus), γ is an incident photon, and n is a liberated neutron.

Materials which are affected in this way generally require an incident photon to have a minimum energy. If there are no photons incident which have an energy of at least that minimum energy there will be no such transition. However, if there are photons present of at least the minimum energy, then such transitions will become possible. The number of neutrons liberated per photon of at least the minimum energy varies depending on at least the so-called cross-section of the material and the energy of the photon.

Thus, by combining the two effects of bremsstrahlung and neutron liberation, it becomes possible to determine if the energy of photons being produced by a linear accelerator is exceeding a neutron liberation minimum energy.

Accordingly, the present invention is directed to a radiotherapy apparatus comprising a linear accelerator for producing a beam of electrons, a target aligned with the electron beam, the target being capable of producing photons when electrons are incident thereon, and a material which is capable of producing neutrons when photons of sufficient energy are incident thereon, a neutron detector capable of providing a signal to a control means of the linear accelerator, the control means being capable of varying the energy of the electrons of the electron beam.

If the electrons generated by the linear accelerator have sufficient energy to produce photons which have at least the minimum energy required to liberate neutrons from the material, then the neutron detector is likely to detect some of the liberated neutrons. If the neutron radiation detected meets a predetermined threshold then the neutron detector will pass a signal to the control means. If radiation detected does not meet that predetermined threshold, then no such signal will be passed. That information, i.e. a lack of that signal, is then used by the control means as a cue to increase the energy of the electrons generated by the linear accelerator.

A second detection threshold may be set, so that the neutron detector may provide a second predetermined signal to the control means if radiation is detected above the second detection threshold. A second predetermined signal received by the control means would result in a reduction in the energy of the electrons generated by the linear accelerator. Such an arrangement is aimed at ensuring that the radiotherapy apparatus does not provide too high a maximum dose level.

The neutron detector and control means thus provide a feedback mechanism to ensure that the output of the radiotherapy apparatus is kept at the desired level and thus that the maximum dose level is as expected.

The target may be constructed of the material. This means that no additional components are required to be placed within the electron beam or the photon beam generated by the linear accelerator. Other parts of the radiotherapy apparatus may be constructed of the material, such as collimator leaves. Using the material in other parts of the apparatus increases the likelihood of neutron liberation, because the photons generated in the target quickly leave the target, but may hit and interact with other parts of the apparatus.

The material may be tungsten, having element symbol W. Naturally-occurring tungsten generally comprises more than one isotope. For the purposes of neutron liberation, the most important isotopes are $^{184}$W and $^{186}$W, which have neutron liberation threshold energies of 7.42 and 7.27 MeV, respectively. $^{182}$W has a neutron liberation threshold of 7.99 MeV. If tungsten is used, then there is an added advantage that no additional neutrons will be produced beyond those which are produced by an existing tungsten target. As neutrons are generally regarded as an undesirable by-product of linear accelerators, it is generally regarded as advantageous to minimise their production.

Thus, when tungsten is used as the material, it may produce neutrons when photons of at least 7.2 MeV are incident thereon.

Other materials are available from which neutrons may be liberated when incident photons of a suitable energy are provided. Different suitable materials can produce neutrons at different energies of photons. For example, beryllium and deuterium have relatively low threshold energies; tantalum-181 has a threshold energy of 6.19 MeV. For controlling linear accelerators which are aimed at producing photons of above the threshold energy of tungsten (7.2 MeV) then different materials may be required. A radiotherapy apparatus may include more than one suitable material for detecting photon energies at different thresholds. However, the additional production of neutrons associated with adding further materials is not preferred. It may be that in the future an improved means for re-absorbing any additional neutrons is developed; in that situation further neutron-producing materials may be considered safe. A proposed location for the material or more than one material is within or adjacent to a beam filter carousel of a radiotherapy apparatus. This area of a radiotherapy apparatus often has a relatively high photon flux, which may make it suitable for the location of suitable material(s). In many accelerators mechanisms exist for moving the beam filter carousel when different energies are selected. Hence it is possible to use different material with the correct gamma-n threshold in the different beam filter carousel positions.

The neutron detector should preferably be placed away from the electron and photon beams produced by the linear accelerator and target. This avoids as far as possible activation of the neutron detector by other non-neutron radiation. The neutron detector may furthermore be placed with a metal mass between it and the electron and photon beams. Due to the transparency of many materials to neutrons, the neutron detector need not be placed in very close proximity to the rest of the radiotherapy apparatus. Lead shielding, for example, which is often used to shield against electromagnetic and charged radiation, is relatively transparent to neutrons. Concrete, however, is a good neutron absorber.

The neutron detector may be a $^3$He (helium-3) proportional neutron detector surrounded by a moderator. A moderator slows down incident neutrons so that they may more easily be detected. A $^3$He neutron detector works because the $^3$He nucleus has a high cross-section for thermal (i.e. relatively slow moving) neutrons. On interaction with a neutron, $^3$He may be split into $^1$H and $^3$H ions, the charge of which can be detected by suitable electronic circuitry. The moderator may be polyethylene and may be formed as substantially a sphere. A preferred moderator is a sphere of approximately 12 cm in diameter. Other neutron detectors may be suitable, for example a $BF_3$ (boron trifluoride) detector. While a $^3$He detector is preferred due to its sensitivity, as the detection of neutrons and related control of linear accelerator energy output is a relatively long-term process, a detector with a lower sensitivity may be suitable even if not preferred.

The control means may modulate the output of the linear accelerator by varying the strength of a radio-frequency electromagnetic field applied to the linear accelerator or by varying the beam current injected into the linear accelerator, or by varying both. Depending on the details of the accelerator other means to vary the energy of the beam may also be possible, the system design will usually choose to use a method appropriate for that accelerator design.

The control means may increase the energy of the electrons of the electron beam of the linear accelerator if the predetermined signal is not received from the neutron detector.

The increase in output may be a pre-determined percentage of the maximum output of the linear accelerator.

The neutron detector may provide a second predetermined signal to the control means if the detected incident radiation rises above a second predetermined level.

The control means may decrease the energy of the electrons of the electron beam of the linear accelerator if the second predetermined signal is received from the neutron detector.

The apparatus and method described herein are intended to supplement existing energy output control means. The present invention relates to a relatively long-term calibration aimed at ensuring that a linear accelerator is kept at a predictable and stable energy output or gold standard. This is aided by the fact that energy is being compared to a basic physical parameter (the gamma-n threshold energy) which is an independent reference from the accelerator own servo system.

The present invention also provides a tool for providing information to a control means of a radiotherapy apparatus, the tool comprising a neutron detector, a count measurement means and a data logging device.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
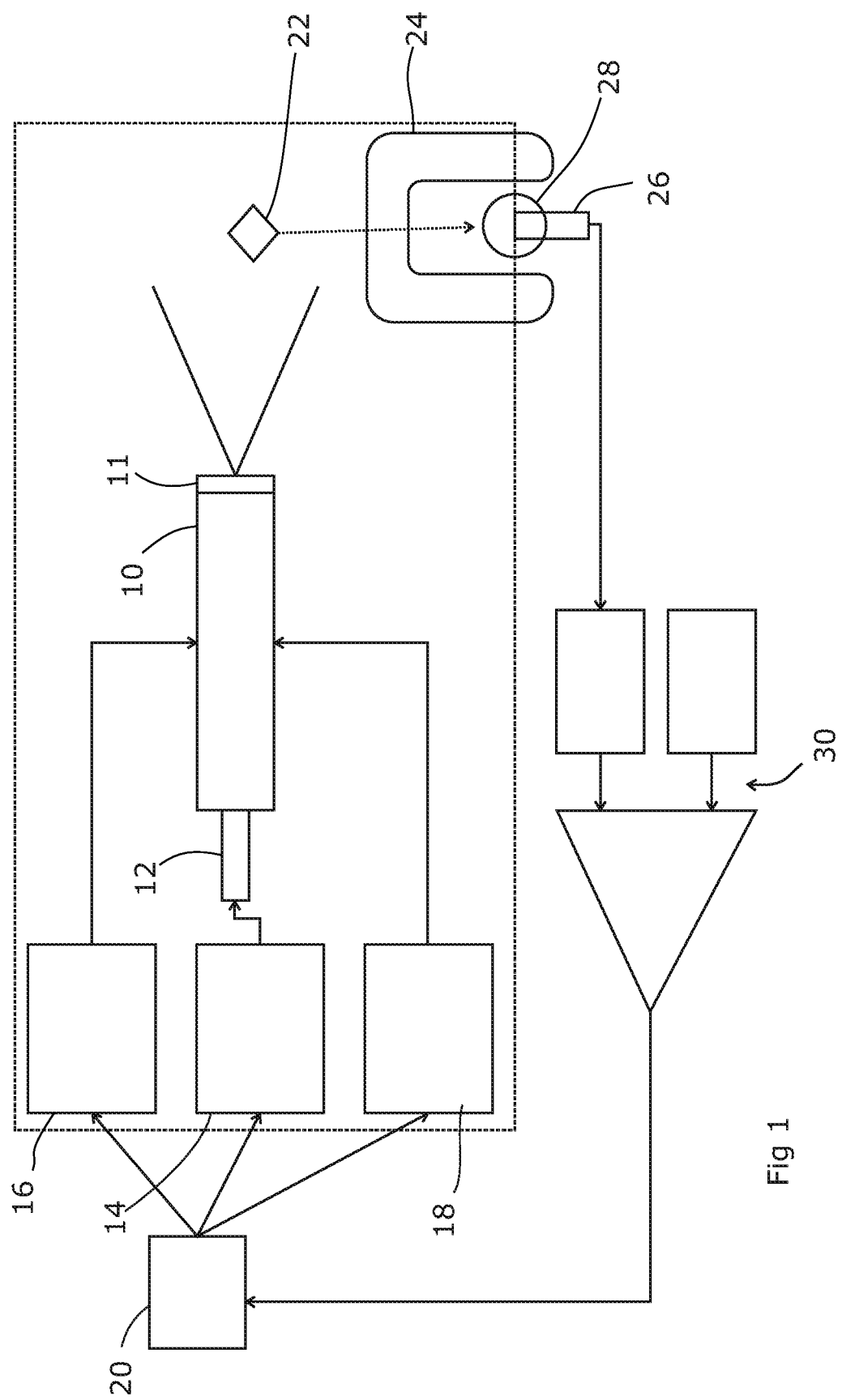
FIG. 1 is a block diagram showing the interaction of different parts of a radiotherapy apparatus according to the present invention.

FIG. 1 shows a radiotherapy apparatus in which a linear accelerator 10 is provided with electrons by an electron gun 12. The gun 12 is provided with electrical current and controlled by a gun current controller 14. The accelerator 10 itself can be controlled by signals from a radio frequency controller 16 and/or an automatic frequency controller (AFC) 18. The gun current controller 14, the radio frequency controller 16 and the AFC 18 may all be provided with signals by a control means 20. A target 11 is provided which may be aligned with the electron beam produced by linear accelerator 10. The target 11 is capable of producing photons (for example, x-rays) when electrons are incident thereon. An N-gamma material 22 is provided which may act as a flattening filter. The N-gamma material 22 may be tungsten. There is further provided an x-ray shield 24 and a neutron detector 26 within a moderator sphere 28. The neutron detector 26 is in turn connected to a comparator means 30 which is further connected to the control means 20.

The comparator means 30 is shown with its usual circuit-diagram symbol. However, it should be noted that the comparator itself may be implemented digitally within another electronic circuit or in software. The control means 20 may be substantially implemented in software, and the comparator means 30 may be integrated within the control means 20.

In use, a beam of electrons produced by the linear accelerator 10 may strike the target 11. The target 11 generates x-rays when the electron beam is incident thereon. The x-rays generated by the target 11 may strike the N-gamma material 22, incident x-rays may in turn liberate neutrons from the N-gamma material 22. If neutrons are liberated in the direction of the neutron detector 26, they may be slowed down by the moderator sphere 28. The neutron detector 26 is shielded from x-ray by an x-ray shield 24. An incident neutron may cause the neutron detector 26 to record that incidence by generating a signal which is in turn transmitted to the comparator means 30. The comparator means 30 compares the signal from the neutron detector with a pre-determined reference level and in turn passes a signal to the control means 20. The control means 20 is pre-programmed so that, by taking the signal from the comparator means 30 or directly from the neutron detector 26, and providing a signal to the gun current controller 14, the radio frequency controller 16 and/or the AFC 18, it can vary the output of electrons from the linear accelerator 10.

Figure 2:
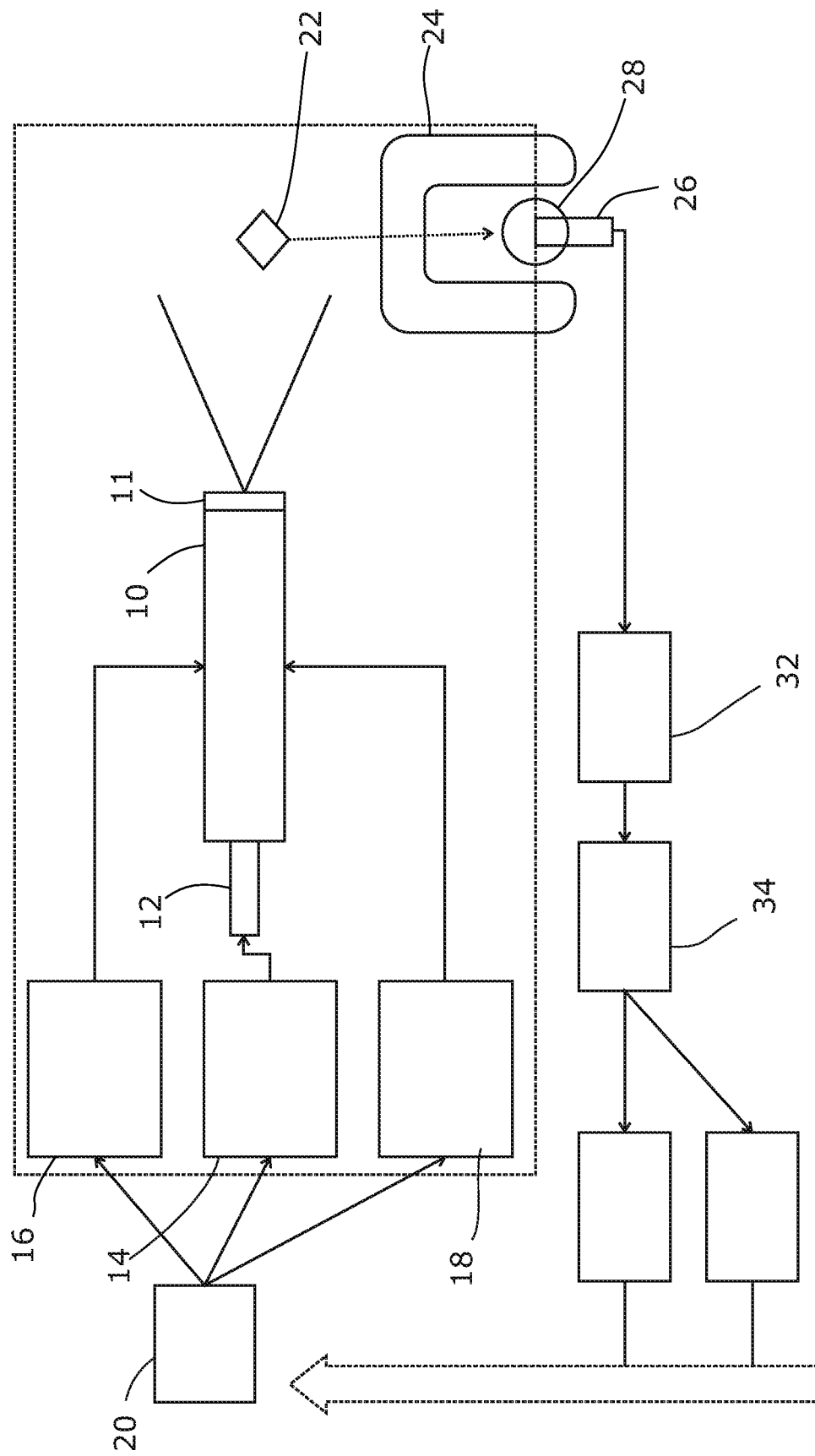
FIG. 2 is a block diagram showing the interaction of different parts of an alternative radiotherapy apparatus according to the present invention.

Turning to FIG. 2, a radiotherapy apparatus in which a linear accelerator 10 is provided with electrons by an electron gun 12. The gun 12 is provided with electrical current and controlled by a gun current controller 14. The accelerator 10 itself can be controlled by signals from a radio frequency controller 16 and/or an automatic frequency controller (AFC) 18. The gun current controller 14, the radio frequency controller 16 and the AFC 18 may all be provided with signals by a control means 20. A target 11 is provided which may be aligned with the electron beam produced by linear accelerator 10. The target 11 is capable of producing photons (for example, x-rays) when electrons are incident thereon. An N-gamma material 22 is provided which may act as a flattening filter. The N-gamma material 22 may be tungsten. There is further provided an x-ray shield 24 and a neutron detector 26 within a moderator sphere 28.

The neutron detector 26 is in turn connected to a count measurement means 32 which is further connected to a data logging means 34. The information collected and collated by the count measurement means 32 and data logging means 34 may be provided to a local technician to assist with adjusting the parameters of the control means 20, or to the manufacturer for provision of adjusted parameters of the control means 20. This arrangement may be more suitable for longer-term calibration and control of energy levels.

Figure 3:
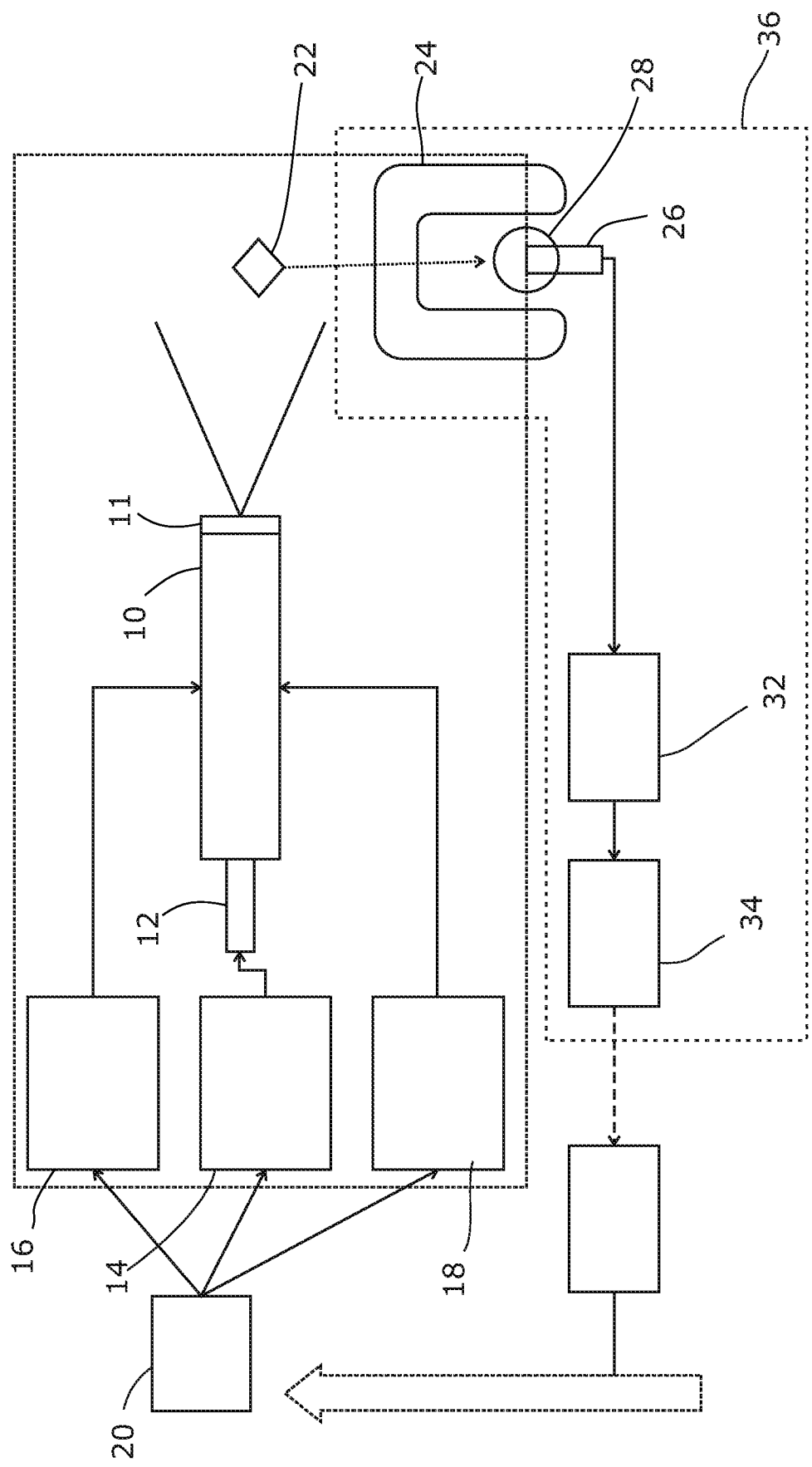
FIG. 3 is a block diagram showing an arrangement in which a radiotherapy apparatus according to the present invention may be embodied in a retro-fitted arrangement.

FIG. 3 shows a similar arrangement to that shown in FIG. 2. However, in the arrangement of FIG. 3 it is envisaged that the neutron detector 26, moderator sphere 28, count measurement means 32 and data logging means 34 are provided as a discrete unit 36. Such a discrete unit could be provided as a quality assurance tool for temporary neutron detection and measurement. This could provide for regular or occasional calibration and control of energy levels of a radiotherapy apparatus. Such a tool could be arranged to provide information to a local technician or the manufacturer, or could be fed directly into the control apparatus 20.

It will of course be understood that many variations may be made to the above-described embodiment without departing from the scope of the present invention.

The invention claimed is:

1. A radiotherapy apparatus, comprising:
    a linear accelerator configured to produce a beam of electrons;
    a target aligned with the electron beam, wherein the target is configured to produce x-ray photons when electrons are incident upon the target;
    a material configured to release neutrons when x-ray photons having energy above a threshold energy level are incident upon the material;
    a neutron detector configured to detect neutron radiation released by the material and to provide a signal based on the detected level of neutron radiation; and
    a controller configured to:
        receive the signal from the neutron detector, and
        if the detected level of neutron radiation is above a predetermined radiation level corresponding to a maximum x-ray dose level of the radiotherapy apparatus, control the linear accelerator to decrease the energy of the electrons of the electron beam.

2. The radiotherapy apparatus according to claim 1, wherein the target comprises the material.

3. The radiotherapy apparatus according to claim 1, wherein the material is tungsten.

4. The radiotherapy apparatus according to claim 1, wherein the material is configured to release neutrons when x-ray photons of at least 7.2 are incident upon the material.

5. The radiotherapy apparatus according to claim 1, wherein the neutron detector is configured to provide a predetermined signal when the neutron detector detects incident radiation above a predetermined background level.

6. The radiotherapy apparatus according to claim 5, wherein the controller is configured to control the linear accelerator to increase the energy of the electrons of the electron beam when the level of neutron radiation detected by the neutron detector is below the predetermined background level.

7. The radiotherapy apparatus according to claim 6, wherein the controller is configured to control the linear accelerator to increase the energy of the electrons by a pre-determined percentage of a maximum x-ray output of the linear accelerator.

8. The radiotherapy apparatus according to claim 1, wherein the neutron detector comprises a Helium-3 proportional counter surrounded by a moderator.

9. The radiotherapy apparatus according to claim 8, wherein the moderator is polyethylene.

10. The radiotherapy apparatus according to claim 8, wherein the moderator is substantially spherical.

11. The radiotherapy apparatus according to claim 1, wherein the controller is configured to modulate output of the linear accelerator by varying the strength of a radio-frequency electromagnetic field applied to the linear accelerator.

12. The radiotherapy apparatus according to claim 1, further comprising:
    a shield arranged between the material and the neutron detector, the shield configured to block incident x-rays and to be transparent to incident neutrons.

13. A method of calibrating the output of a radiotherapy apparatus, the method comprising:
    positioning a neutron detector relative to a linear accelerator and a target such that the neutron detector is clear of electron beams or x-ray photons generated by the linear accelerator or the target, wherein the linear accelerator is configured to produce a beam of electrons, and the target is aligned with the electron beam produced by the linear accelerator and is configured to produce x-ray photons when the electron beam is incident upon the target;

detecting, with the neutron detector, a level of neutron radiation released by a material, wherein the material is configured to release neutrons when x-ray photons having energy above a threshold energy level are incident upon the material; and when the detected level of neutron radiation is above a predetermined radiation level corresponding to a maximum x-ray dose level of the radiotherapy apparatus, controlling the linear accelerator to decrease the energy of the electrons of the electron beam.

14. The method according to claim 13, wherein the calibration occurs continuously during operation of the radiotherapy apparatus.

15. The method according to claim 13, wherein the calibration is effected during a start-up cycle of the radiotherapy apparatus.

16. The method according to claim 13, further comprising:

controlling the linear accelerator to increase the energy of the electrons of the electron beam when the detected level of neutron radiation is below a predetermined background level.

17. The method according to claim 13, wherein controlling the linear accelerator comprises:

varying the strength of a radio-frequency electromagnetic field applied to the linear accelerator.

18. The method according to claim 13, wherein controlling the linear accelerator comprises:

varying a beam current injected into the linear accelerator.

19. The method according to claim 13, further comprising:

arranging a shield between the material and the neutron detector, wherein the shield is configured to block incident x-rays and to be transparent to incident neutrons.

* * * * *

UNITED STATES PATENT AND TRADEMARK OFFICE
CERTIFICATE OF CORRECTION

PATENT NO. : 10,821,305 B2
APPLICATION NO. : 15/598377
DATED : November 3, 2020
INVENTOR(S) : John Allen Page 1 of 1

It is certified that error appears in the above-identified patent and that said Letters Patent is hereby corrected as shown below:

In the Claims

Claim 4, Column 6, Line 31:
"x-ray photons of at least 7.2 are incident upon the material"
Should read:
--x-ray photons of at least 7.2 MeV are incident upon the material--.

Signed and Sealed this
First Day of December, 2020

Andrei Iancu
*Director of the United States Patent and Trademark Office*